(12) United States Patent
DiFoggio et al.

(10) Patent No.: US 7,280,214 B2
(45) Date of Patent: Oct. 9, 2007

(54) METHOD AND APPARATUS FOR A HIGH RESOLUTION DOWNHOLE SPECTROMETER

(75) Inventors: Rocco DiFoggio, Houston, TX (US); Arnold Walkow, Houston, TX (US); Paul Bergren, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 456 days.

(21) Appl. No.: 10/827,948

(22) Filed: Apr. 20, 2004

(65) Prior Publication Data

US 2005/0018192 A1  Jan. 27, 2005

Related U.S. Application Data

(63) Continuation-in-part of application No. 10/162,023, filed on Jun. 4, 2002, now abandoned.

(51) Int. Cl.
*G01J 3/51* (2006.01)
(52) U.S. Cl. ........................ 356/419; 356/416
(58) Field of Classification Search ................ 356/51, 356/416, 418, 419
See application file for complete search history.

(56) References Cited

U.S. PATENT DOCUMENTS

| | | | |
|---|---|---|---|
| 2,834,246 A | 5/1958 | Foskett et al. | |
| RE28,216 E | 10/1974 | Barringer et al. | |
| 3,877,818 A | 4/1975 | Button et al. | |
| 4,167,338 A | 9/1979 | Kraus | |
| 4,326,802 A | 4/1982 | Smith, Jr. et al. | |
| 4,752,129 A | 6/1988 | Izumi et al. | |
| 5,070,245 A | 12/1991 | Rantala et al. | |
| 5,166,747 A | 11/1992 | Schroeder et al. | |
| 5,167,149 A | 12/1992 | Mullins et al. | |
| 5,268,745 A | 12/1993 | Goody | |
| 5,426,297 A | 6/1995 | Dunphy et al. | |
| 5,729,013 A | 3/1998 | Bergren, III | |
| 5,939,717 A | 8/1999 | Mullins | |
| 6,350,986 B1 | 2/2002 | Mullins et al. | |

FOREIGN PATENT DOCUMENTS

EP  1 150 106 A1  10/2001
GB  2 368 391 A  5/2002

*Primary Examiner*—F. L. Evans
(74) *Attorney, Agent, or Firm*—Madan, Mossman & Sriram, P.C.

(57) ABSTRACT

The present invention provides a simple, robust, and versatile high-resolution spectrometer that is suitable for downhole use. The present invention provides a method and apparatus incorporating a spinning, oscillating or stepping optical interference filter to change the angle at which light passes through the filters after passing through a sample under analysis downhole. As each filter is tilted, the color or wavelength of light passed by the filter changes. Black plates are placed between the filters to isolate each filter's photodiode. The spectrometer of the present invention is suitable for use with a wire line formation tester, such as the Baker Atlas Reservation Characterization Instrument to provide supplemental analysis and monitoring of sample clean up. The present invention is also suitable for deployment in a monitoring while drilling environment. The present invention provides a high resolution spectometer which enables quantification of a crude oil's percentage of aromatics, olefins, and saturates to estimate a sample's gas oil ratio (GOR). Gases such as $CO_2$ are also detectable. The percentage of oil-based mud filtrate contamination in a crude oil sample can be estimated with the present invention by using a suitable training set and chemometrics, a neural network, or other type of correlation method.

39 Claims, 10 Drawing Sheets

EXAMPLE SHOWING TWO INTERFERENCE FILTERS SANDWICHED BETWEEN THREE BAFFLES

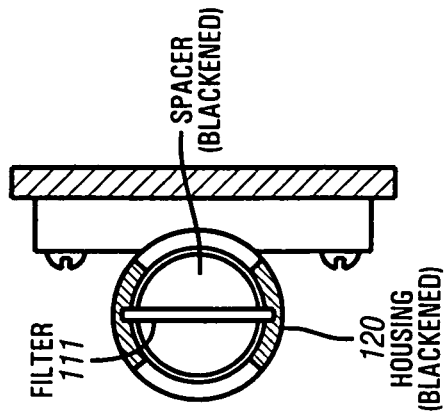
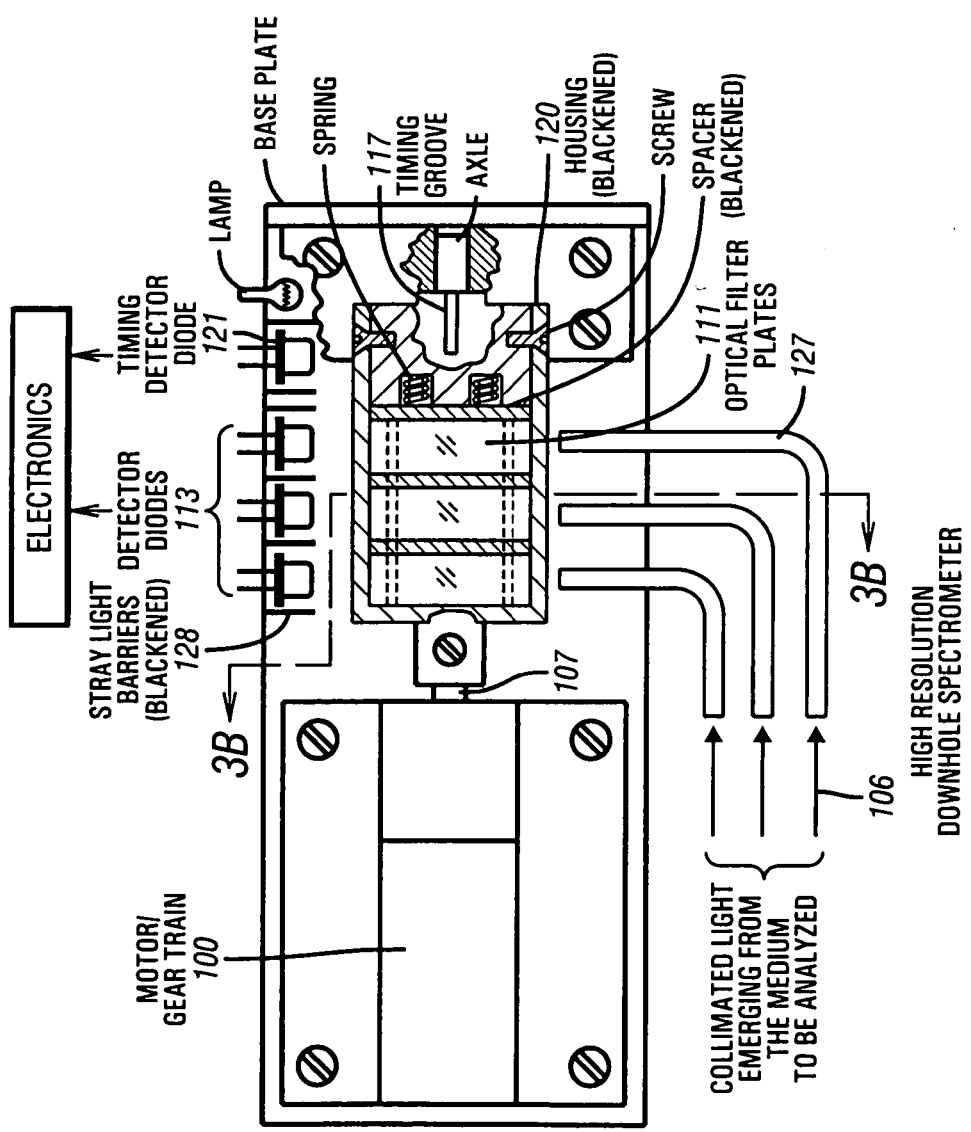

METHOD AND APPARATUS FOR A HIGH RESOLUTION DOWNHOLE SPECTROMETER

CROSS-REFERENCE TO RELATED APPLICATIONS

This application is a continuation in part patent application of U.S. patent application Ser. No. 10/162,023 entitled A Method and Apparatus for a High Resolution Downhole Spectrometer by R. DiFoggio et al., filed on Jun. 4, 2002 now abandoned. This patent application is related to U.S. patent application Ser. No. 10/453,717, entitled "A Method and Apparatus for a Downhole Flourescence Spectrometer" by Rocco DiFoggio, Paul Bergen and Arnold Walkow, filed on Jun. 3, 2003 which is hereby incorporated herein by reference in its entirety. This application is related to U.S. patent application Ser. No. 10/162,030, entitled "A Method and Apparatus for a Derivative Spectrometer" by Rocco DiFoggio, Paul Bergen and Arnold Walkow, filed on Jun. 4, 2002 which is hereby incorporated herein by reference in its entirety. This application is related to the U.S. patent application Ser. No. 10/119,492 filed on Apr. 10, 2002 by Rocco DiFoggio et al., entitled "A Method and Apparatus for Downhole Refractometer and Attenuated Reflectance Spectrometer" which is hereby incorporated herein by reference in its entirety.

BACKGROUND OF THE INVENTION

1. Field of the Invention

The invention pertains in general to a high-resolution downhole scanning spectrometer that is suitable for downhole use and in particular, to a downhole spectrometer that employs spinning, oscillating, or stepping one or more optical interference filters to change the angle at which light passes through them to obtain a higher resolution measurement.

2. Summary of the Related Art

Oil companies take samples from formations to determine the characteristics of the formation. These samples are typically pumped from the formation and initially contain contaminants such as well bore fluid that have invaded the formation. Contaminated samples yield invalid results when trying to determine the properties of a hydrocarbon bearing formation. Thus, oil companies desire an accurate measure of sample contamination percentage in real time as they are pumping sample fluid from a formation so that they can decide when to divert a reasonably pure formation fluid sample into a collection tank. They do not want to pump unnecessarily long and waste very expensive rig time. Conversely, they do not want to pump too little and collect a useless sample. If the contamination is more than about 10%, the sample may be useless.

In such cases, the PVT properties measured in the lab cannot be corrected back to true reservoir conditions because of this excessive contamination. It is therefore necessary to perform measurements downhole to assess the sample contamination and associated merits of information regarding formation properties derived from the downhole sample. One method of investigation comprises using a spectrometer to perform optical measurements on the fluid samples as they are pumped through a sampling instrument and subsequently collected in a downhole environment.

Numerous factors affect downhole spectrometry measurements. In the down-hole environment, photodetectors are utilized and must operate at high ambient temperatures, thus, they are very noisy and generate very little signal. Moreover, dirty or contaminated samples of flowing streams of crude oil containing scatterers such as sand particles or gas bubbles tend to add noise to the system. These scatterers cause the optical spectrum to momentarily "jump" up, appearing darker as the scatterers pass through the sample cell. At high concentrations, these scatterers cause the measured spectrum to jump or rise up repeatedly. To first order, the scattering effect is just a momentary baseline offset. One way to eliminate baseline offset and greatly improve the signal-to-noise ratio of a downhole spectrometer is to collect the derivative of the spectra with respect to wavelength. Derivative spectra can be obtained by modulating the wavelength of light and using a lock-in amplifier.

It is commonplace for spectrometers to disperse white light into its constituent colors. The resulting rainbow of colors can be projected through a sample and onto a fixed array of photodetectors. Alternatively, by rotating a dispersive element (i.e. grating, prism), the rainbow can be mechanically scanned past a single photodetector one color at a time. In either case, an operator can obtain a sample's darkness versus wavelength, in other words, its spectrum.

Photodetectors and their amplifiers almost always have some thermal noise and drift, which limit the accuracy of a spectral reading. As operating temperature increases, noise and drift increase dramatically at the same time that photodetector signal becomes significantly weaker. If an operator oscillates the wavelength (color) of light about some center wavelength, then the operator can reject most photodetector and amplifier noise and drift by using an electronic bandpass filter, centered at the oscillation frequency. The operator can further reject noise by using a phase-sensitive ("lock-in") amplifier that not only rejects signals having the wrong frequency but also rejects signals having the correct frequency but having no fixed phase relationship (indicative of noise) relative to the wavelength oscillation. A lock-in amplifier can improve signal to noise by as much as 100 db, which is a factor of $10^{100\ db/10}$ or 10 billion.

The output of the lock-in amplifier used in this procedure is proportional to the root-mean-square (RMS) amplitude of that portion of the total signal, that portion being at the same frequency and having a fixed phase relationship relative to the optical frequency being observed. The more that the darkness of the sample changes with color, the larger importance this RMS value will have to the operator. In other words, the output of lock-in amplifier for a system with an oscillating-wavelength input is proportional to the derivative of the spectrum (with respect to wavelength) at the center wavelength of the oscillation.

U.S. Pat. No. 3,877,818, Photo-Optical Method for Determining Fat Content in Meat, issued Apr. 15, 1975, to Button et al. discloses an apparatus in which light reflected off the surface of a piece of meat passes through a lens and strikes an oscillating mirror. The angle of reflection of the light reflected off this mirror varies with the mirror's oscillation. Light reflected from the mirror strikes a stationary interference filter and onto a photodetector. The color transmitted through the interference filter varies slightly with the angle of incidence of the light beam striking it. Thus, the wavelength of radiation passing through the filter oscillates over a narrow range about the wavelength for fat absorption of meat and can be used to determine the fat content of the meat. Button et al. does not enable the possibility of a full rotation or control of the angular deviation.

Current down-hole "spectrometers" (for example, Schlumberger's Optical Fluid Analyzer (OFA) and Baker Atlas' SampleView[SM]) utilize discrete filter photometers.

Each optical channel is achieved by filtering light for each individual channel through an optical filter of a color corresponding to the optical channel. Therefore, the wavelength coverage of such a discrete spectrometer is not continuous, but discrete. The discrete spectrum has gaps that go from the center wavelength of one discrete optical filter to the center wavelength of the next discrete optical filter. These gaps can be large ones of 100 to 200 nm or more in wavelength coverage. The channels of such devices are broad. In the current down-hole spectrometer, all hydrocarbon peaks are lumped into one broad channel centered at 1740 nm, with a Full Width at Half Maximum (FWHM) of 32 nm.

The down-hole environment is difficult for operating sensors. Reasons include limited space within a tool's pressure housing, elevated temperatures, and the need to withstand shock and vibration. Components such as motors, interference filters, and photodiodes in the logging tools, are already fabricated and available to withstand temperature, shock and vibration of the downhole environment. Thus, it is possible to manufacture this spectrometer into a small enough package in order to squeeze into the available space inside the current SampleView$^{SM}$ module.

For comparison, many laboratory spectrometers use a grating to disperse the light into its constituent colors. However, almost all gratings are an epoxy-on-glass replica of a master grating. These epoxy replicas soften and creep at high temperature, which causes a distortion in the spectrum and a loss in light intensity. Moreover, the price of an all-glass master grating ($50-100K) is prohibitively expensive.

Known laboratory spectrometers typically utilize Fourier Transform (FT) spectroscopy which are unsuitable for down-hole applications. FT spectrometers are large (2-3 feet long, 1-2 feet wide), heavy (200-300 lbs), mechanically and electronically complicated, and must maintain perfect alignment of all their optical components to work properly, which is why they are typically built on a very rigid framework. Thus, there is a need for a high-resolution spectrometer which is small enough and robust for operation in a down-hole environment.

SUMMARY OF THE INVENTION

The present invention provides a simple, robust, and versatile high-resolution spectrometer that is suitable for downhole use. The present invention provides a method and apparatus incorporating a spinning, oscillating or stepping optical interference filter to change the angle at which light passes through the filters after passing through a sample under analysis downhole. As each filter is tilted, the color or wavelength of light passed by the filter changes. Black plates are placed between the filters to isolate each filter's photodiode. The spectrometer of the present invention is suitable for use with a wire line formation tester, such as the Baker Atlas Reservation Characterization Instrument to provide supplemental analysis and monitoring of sample clean up. The present invention is also suitable for deployment in a monitoring while drilling environment. The present invention provides a high resolution spectometer which enables quantification of a crude oil's percentage of aromatics, olefins, and saturates to estimate a sample's gas oil ratio (GOR). Gases such as $CO_2$ are also detectable. The percentage of oil-based mud filtrate contamination in a crude oil sample can be estimated with the present invention by using a suitable training set and chemometrics, a neural network, or other type of correlation method.

BRIEF DESCRIPTION OF THE DRAWINGS

FIGS. 3A and 3B illustrate a more detailed schematic representation of an embodiment of the present invention showing a time groove;

DETAILED DESCRIPTION OF AN EXEMPLARY EMBODIMENT

Figure 1:
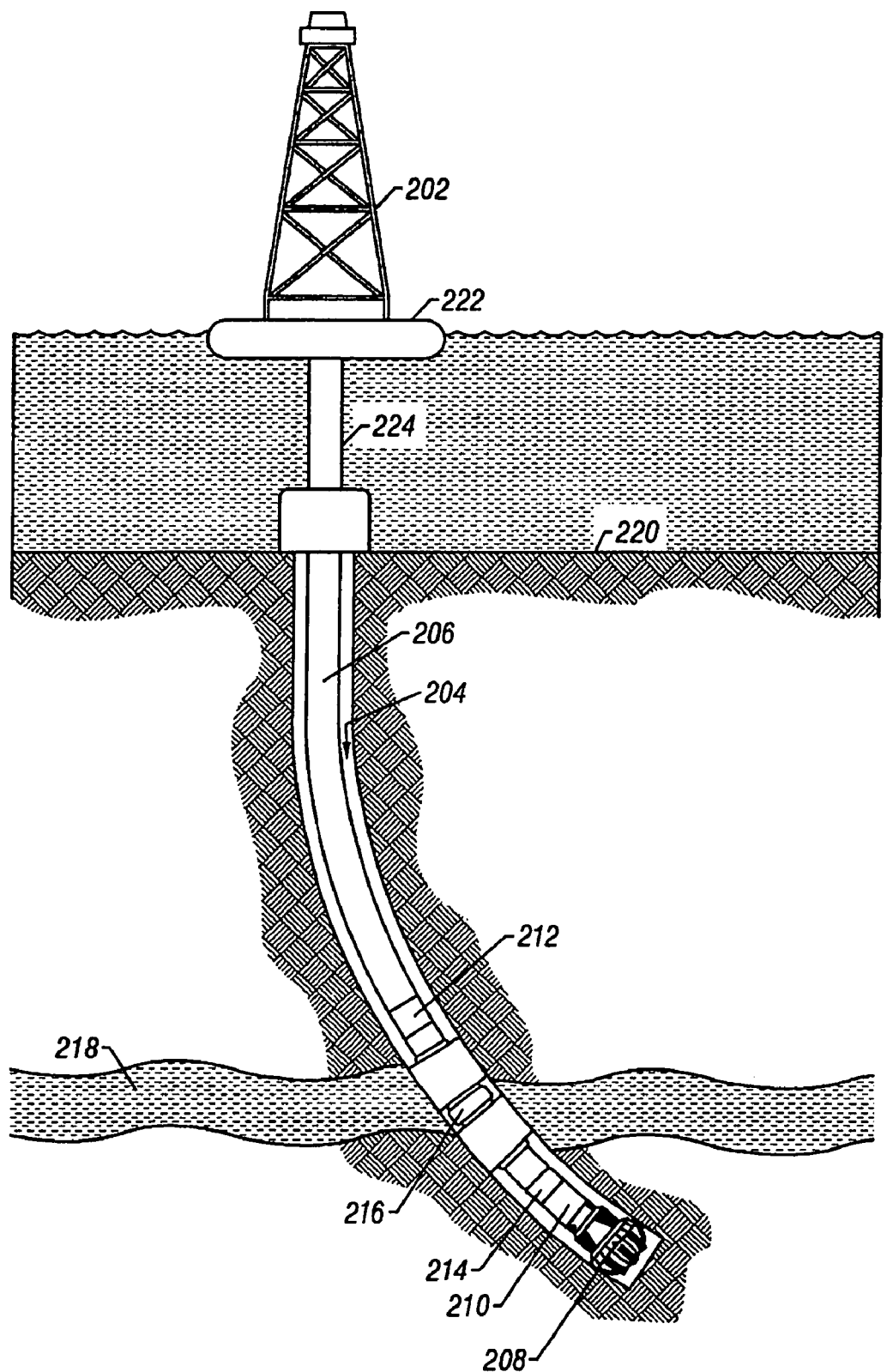
FIG. 1 is an illustration of the present invention deployed in a downhole environment in a bore hole.

FIG. 1 illustrates an embodiment of the present invention deployed in a borehole. The present invention is suitable for deployment in either a wire line, slick line or monitoring while drilling environment. FIG. 1 illustrates a preferred embodiment of the present invention deployed in a monitoring while drilling operation.

Turning now to FIG. 1, FIG. 1 is a drilling apparatus according to one embodiment of the present invention. A typical drilling rig 202 with a borehole 204 extending there from is illustrated, as is well understood by those of ordinary skill in the art. The drilling rig 202 has a work string 206, which in the embodiment shown is a drill string. The drill string 206 has attached thereto a drill bit 208 for drilling the borehole 204. The present invention is also useful in other types of work strings, and it is useful with a wireline, jointed tubing, coiled tubing, or other small diameter work string such as snubbing pipe. The drilling rig 202 is shown positioned on a drilling ship 222 with a riser 224 extending from the drilling ship 222 to the sea floor 220. However, any drilling rig configuration such as a land-based rig may be adapted to implement the present invention.

If applicable, the drill string 206 can have a downhole drill motor 210. Incorporated in the drill string 206 above the drill bit 208 is a typical testing unit, which can have at least one sensor 214 to sense downhole characteristics of the borehole, the bit, and the reservoir, with such sensors being well known in the art. A useful application of the sensor 214 is to determine direction, azimuth and orientation of the drill string 206 using an accelerometer or similar sensor. The bottom hole assembly (BHA) also contains the formation test apparatus 216 of the present invention, which will be described in greater detail hereinafter. A telemetry system 212 is located in a suitable location on the work string 206 such as above the test apparatus 216. The telemetry system 212 is used for command and data communication between the surface and the test apparatus 216.

Figure 2:
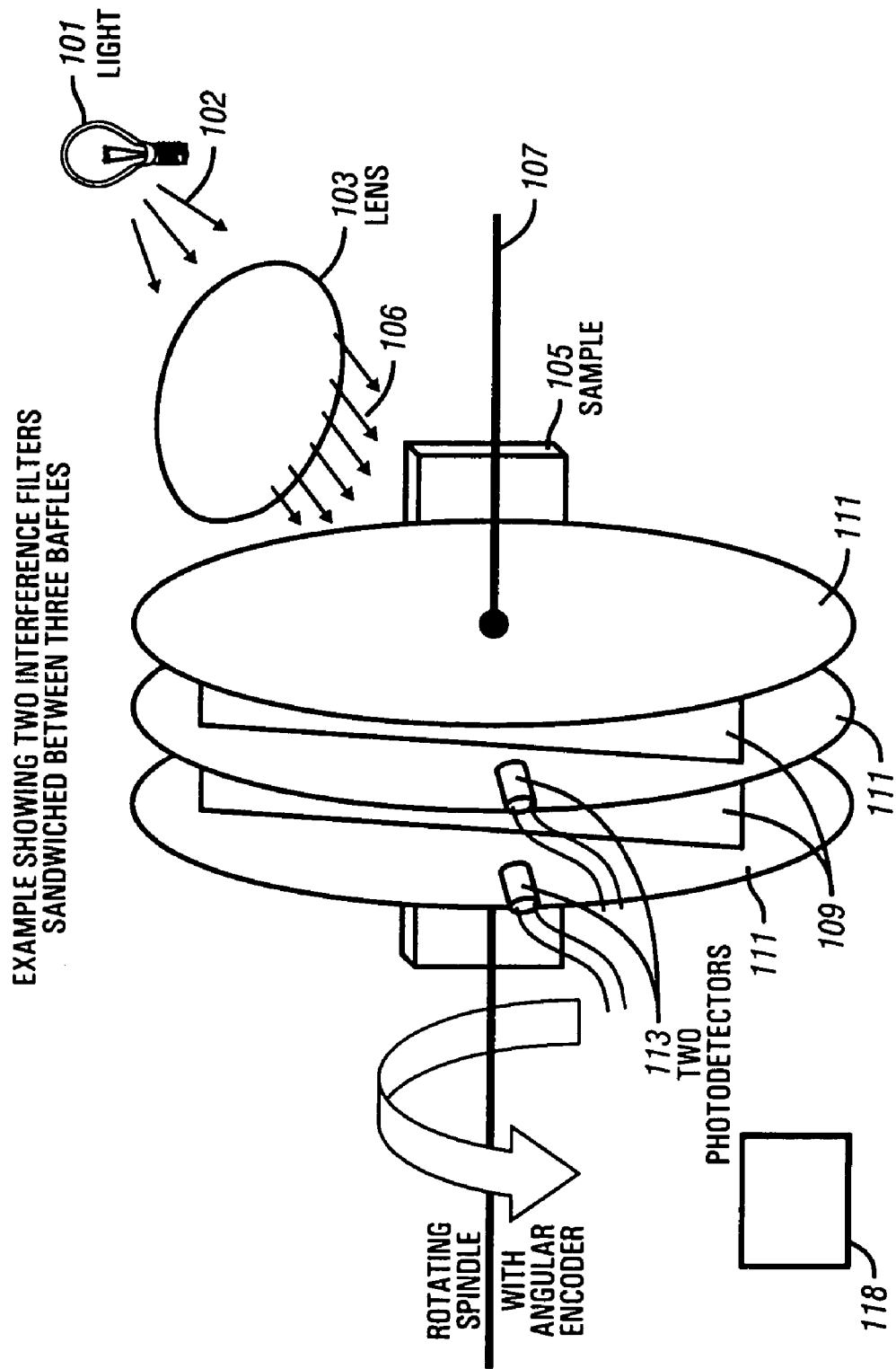
FIG. 2 is a schematic representation of an embodiment of the present invention.

FIG. 2 illustrates an embodiment of the invention. A light source 101 (e.g. a tungsten light bulb) provides a beam of light 102 which is targeted to be incident upon and through a collimating lens 103 onto a sample 105 which contains a sample to be analyzed by the present invention. In an embodiment, formation fluid samples flow through sample chamber (chamber not shown for simplicity) and are tested for purity or other properties by the present invention. The collimated light is shown upon and transmitted through the sample 105 and towards a filter assembly. The filter assembly comprises one or more optical filters 109 positioned between baffles 111 and mounted on a rotating spindle 107. FIG. 2 illustrates, for example, an assembly in which two optical filters 109 are positioned between three baffles 111. A rotating spindle 107 is oriented with its axis generally perpendicular to the direction of the light transmitted from the sample and rotates about its axis. The one or more optical filters 109 are mounted on the spindle so that, in one angular orientation of the spindle, the plane of the filters are generally perpendicular to the light transmitted from the sample. As the spindle rotates, light 106, after passing through lens 103, impinges on the face of interference filters 109 at incident angles other than normal. A processor 118 controls data acquisition and analysis for the present invention.

Light transmitted through the interference filters 109 is transmitted to one or more photodetectors 113 (e.g., InGaAs photodetectors). The filters are specified according to their center wavelength for transmitted light at normal incidence. However, their center wavelength for transmitted light is different at non-normal incidence. As one tilts a single-color optical interference filter so that white light no longer strikes the filter perpendicular to its face, the color (that is, wavelength) of the light that is transmitted, shifts from its original color to a shorter wavelength. The greater the angle of tilt of an interference filter away from normal incidence, the greater the shift in the wavelength. For example, tilting a yellow ($\lambda$=590 nm) interference filter, the transmitted light shifts away from yellow. With sufficient tilt from normal, the light transmitted through the "yellow" filter shifts to green ($\lambda$=525 nm). Interference filters are chosen according to desired applications. As an example, a $\lambda$=1800 nm wave length interference filter, when rotated, transmits over a broad range of wavelengths so that the range of wavelengths scans past the hydrocarbon absorbance peaks located around $\lambda$=1760 nm.

The external surfaces of the housing and the spacer disks and stray light barriers are optically black to prevent stray light from interfering with the light to be measured. One exception is a narrow machined timing groove 117 as shown in FIG. 3 and a second timing groove on the opposite side of the housing to obtain two timing marks per revolution and to select which filter is being read and from which side it is read or alternatively to average the readings through both sides. Additional timing grooves are provided for added angular displacement resolution for rotational position determination. The light illuminates the timing groove when it appears, and a timing detector diode senses the light from the timing groove at which time the data acquisition electronics are alerted to obtain and analyze data.

The present invention provides for full exposure of each optically isolated filter during rotation around an exposed center of rotation. Each filter is held by its edges to avoid shadowing the filter's center of rotation. The present invention enables full analysis and expanded capability to read only a designated side of each filter or an average of both sides. Four spectral scans per revolution are provided, which are selectable so that any scan can be selected separately or two or more scans can be averaged.

For collimated light that is incident on an interference filter, the transmitted wavelength is given by the following formula, $$\lambda=\lambda_0[1-(n_0/n^*)^2 \sin^2\theta]^{1/2} \quad (1)$$

where $\lambda$ is the central wavelength of the filter for light incident at an angle $\theta$ from normal, $\lambda_0$ is the central wavelength of the filter for light at normal incidence ($\theta$=0), $n_0$ is the refractive index of medium surrounding the filter (in the present example of the invention, the medium is air so $n_0$=1), $n^*$ is the effective refractive index of the filter, and $\theta$ is the angle from normal incidence ($\theta$=$\omega$t, where $\omega$=angular velocity, t=time). The wavelength shift of the filter depends only on the angle by which the incident light beam is rotated away from normal incidence, regardless of whether that rotation is positive or negative. Thus, it is expected that oscilloscope displays are symmetrical (a mirror image) about the center of each spectrum. This center spectrum corresponds to a filter's nominal center wavelength, for example, $\lambda$=1800 nm. The further right or left of the center spectrum, the shorter the wavelength. Since the filter rotates on its spindle and at a constant rate so that angle depends on time, then the wavelength, $\lambda$, decreases with the absolute value of time, $|t-t_0|$, where $t_0$ is the moment in time at which the filter is centered on its central wavelength.

Typically, the range of shift for the wavelength of light transmitted from the filter is about 100 nm. As the angle of rotation increases, the filter becomes tilted with respect to the incident angle of light to the extent that substantially no light goes through the face of the filter. Instead, substantially all of the light incident on the filter is reflected off the filter face, because it is striking it at such a glancing obtuse angle. At a sufficiently large rotation angle, incident light runs into the edge of the filter or into the edge of the filter holder.

In one mode of the invention, by spinning or oscillating such an interference filter, it is possible to quickly and continuously sweep through a range of wavelengths from the original center wavelength to a new center wavelength, which is about 100 nm shorter than the center wavelength for a given filter. To increase the range of wavelengths that are scanned by the present invention, the present invention preferably comprises several strips of interference filters (having different central wavelengths) side by side, but separated by thin black disks (baffles) 111. These interference filter strips rotate together as shown conceptually in FIG. 2. The thin black disks enable a photodiode placed between a pair of black disks to monitor the light transmitted by a single filter without seeing light transmitted by a neighboring filter.

A more detailed depiction of an embodiment is shown in FIG. 3. As shown in FIG. 3A, a motor and gear train assembly 110 provides rotational force to spindle 107 which in turn rotates housing 120 and filter plates 111. Stray light barriers 128 are provided between photodetector diodes 113 to prevent leakage between individual diodes 113 and associated channels of information. A timing groove 117 is illuminated by a lamp 123 to facilitate rotational and angular cracking of housing and filter 111. Light 106 emerging from sample to be analyzed is run through light tubes 127 to moving filter 111. A side view of housing 120 is shown in FIG. 3B.

In another mode of the invention, the filter oscillates to scan over an absorption peak (e.g., λ=1667 nm for methane, or λ=1957 nm for carbon dioxide) in order to determine the difference in transmitted light intensity on-peak versus off-peak. This difference in on/off peak readings (or the amplitude of the resulting AC signal if done rapidly) is generally proportional to the concentration of the absorbing species.

For light that is incident at an angle, which is not normal to the filter, light still emerges from the filter parallel to the original beam (due to normal incidence). However, the path of the filtered light is translationally displaced (offset) from the path of the light emerging from the non-rotated filter. Therefore, a sufficiently large converging lens is provided to collect the light, regardless of offset, which facilitates the operation of the invention in the present example. Also, the optical band pass of the filter changes with the angle of incidence. The band pass of the tilted filter is wider than the band pass of the un-tilted filter. Note that color shifting with angle only occurs for optical filters that are based on interference. Color shifting does not occur for filters that are inherently colored.

The present invention enables the detection and analysis of small peaks or perturbations in the spectral response for a sample including the case of a small peak sitting on the shoulder of a larger peak. For example, the present invention may either step, oscillate or spin the interference filter. In the case of a small perturbation or peak upon the shoulder of another peak, the present invention may step between two colors, one that is on the peak and one off of the peak. In this way, the present invention can detect small or overlapping peaks, which with previous downhole spectroscopy techniques and equipment, were lumped into a single broad and undiscriminating hydrocarbon band. For example, in the absorbance spectrum, the methane peak is a side peak on the main hydrocarbon peak. The present invention enables detection of this small methane peak by stepping between the methane peak at 1667 nanometers and a lower off peak color, for example 1600 nanometers. The present invention provides a stepper motor to step between positions or colors for the interference filter. By stepping between the on peak 1667 nm and off peak 1600 nm the present invention is able to detect the small peak at 1667 nm for methane. Alternatively, the present invention can quantity the amount of methane by applying chemometrics, neural networks, or other soft modeling techniques to the continuous spectra obtained by the present invention for a known training set of samples.

The high-resolution spectrometer of the present invention enables determination of the percent of aromatics, olefins, saturates and contaminants in a sample. The high-resolution spectrometer of the present invention enables detection and analysis of peaks that were heretofore undetectable with known downhole spectrometer technology. Known downhole spectrometers group together most first-overtone hydrocarbon peaks into a single hydrocarbon channel without resolving the small or overlapped peaks within this channel, which can provide information about concentrations of aromatics, olefins, saturates, filtrate contamination, and so on. In an embodiment, the present invention collects high resolution spectra for a training set of known samples. Applying chemometrics to these spectra, the present example of the invention develops mathematical models, which enables the present invention to estimate the corresponding properties of unknown samples directly from their high resolution spectra. Chemometrics, neural networks, and other soft modeling techniques let us skip the intermediate steps of identifying chemical meanings for individual spectral peaks and the reasons that these peaks shift or overlap with other peaks. That is, soft modeling techniques enable the present invention to take high resolution spectra of a known training set and directly model the chemical or physical properties of interest. One property of interest is filtrate contamination. Known sampling techniques do not currently provide a direct measurement of the percentage of filtrate contamination in a formation fluid sample.

Figure 9:
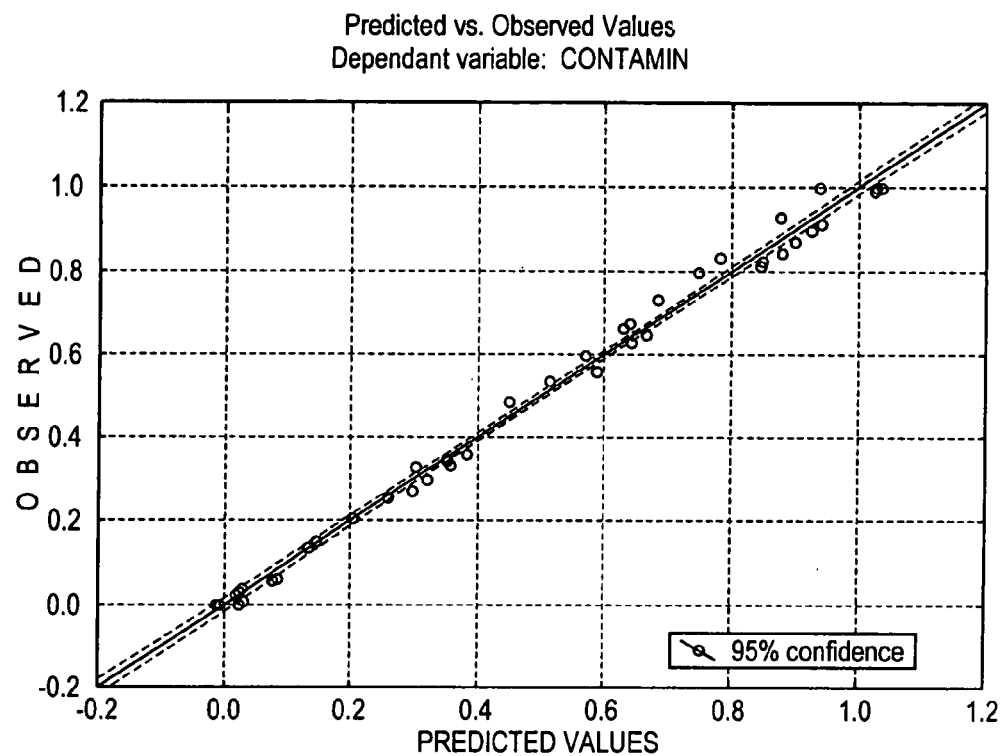
FIG. 9 shows the correlation ($r^2$=0.993) of filtrate contamination to two wavelengths of a training set of forty-three 2-wavenumber-resolution spectra.

FIG. 9 plots a correlation ($r^2$=0.993) found between the fraction of filtrate contamination and some very-high resolution (2-wavenumber) spectra of 3 crude oils (representing low, medium and high viscosity), 4 synthetic mud filtrates, and 36 simulated mixtures of a crude oil with a mud filtrate. These Attenuated Total Reflectance (ATR) spectra were collected on a commercial laboratory spectrometer made by Nicolet. These spectra have higher resolution than one would be able to obtain with the methods of the present invention. The spectra span the fundamental frequencies of molecular vibration.

Note, that with a single equation, we were able to quantify the percentage of filtrate contamination regardless of which filtrate was contaminating which crude oil. Apparently, underlying chemical differences between filtrates and the crude oils can be detected and quantified. Here, the correlation is to a region around 3032 wavenumbers. A wavenumber is one reciprocal centimeter. Therefore, 3032 wavenumbers is $10^7/3032$=3298 nm because there are 10 million nanometers in a centimeter.

In FIG. 9, we see that the fraction of filtrate contamination is given by the equation:

$$f_C = -2.25 - 1072.71 * A\_3037.38 \text{ cm}^{-1} + 1130.20 * A\_3027.74 \text{ cm}^{-1}$$

Because this correlation equation is based on the absorbance at two wavelengths (3037.38 cm$^{-1}$ and 3027.74 cm$^{-1}$) that are close to one another and whose regression coefficients are approximately equal in magnitude but opposite in sign (−1072.71 and 1130.20) it is, in essence, a correlation to the slope of the spectrum at the midpoint between the two wavelengths. It may be a correlation to the absence of aromatics in the filtrates because, for environmental reasons, the base oils for these synthetic muds are generally made without aromatics. The aromatic C—H stretch peak occurs from 3125-3030 cm$^{-1}$ whereas the non-aromatic C—H stretch occurs around 2940-2855 cm$^{-1}$. Thus, it appears that the slope of spectrum in the region where aromatic peaks end and non-aromatic peaks begin is a way to directly measure the filtrate contamination independent of the filtrate, the crude, or any visible colors of either (this wavelength range is far past that of visible colors or any electronic transitions). It is expected that overtones (somewhere in the 1600-1800 nm range) of these fundamental bands (3125-2855 cm$^{-1}$) will have corresponding sensitivity to the underlying chemical differences between filtrates and crude oil.

Figure 10:
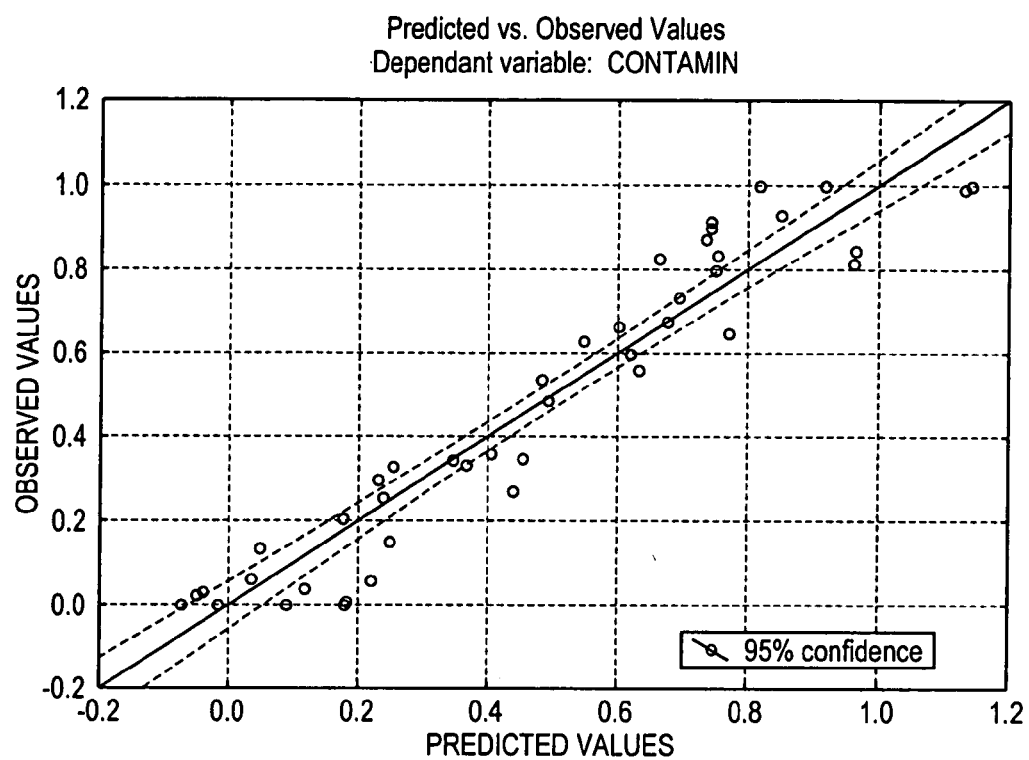
FIG. 10 shows the correlation ($r^2$=0.908) of filtrate contamination to two wavelengths of a training set of forty-three 22-wavenumber-resolution spectra.
Figure 11:
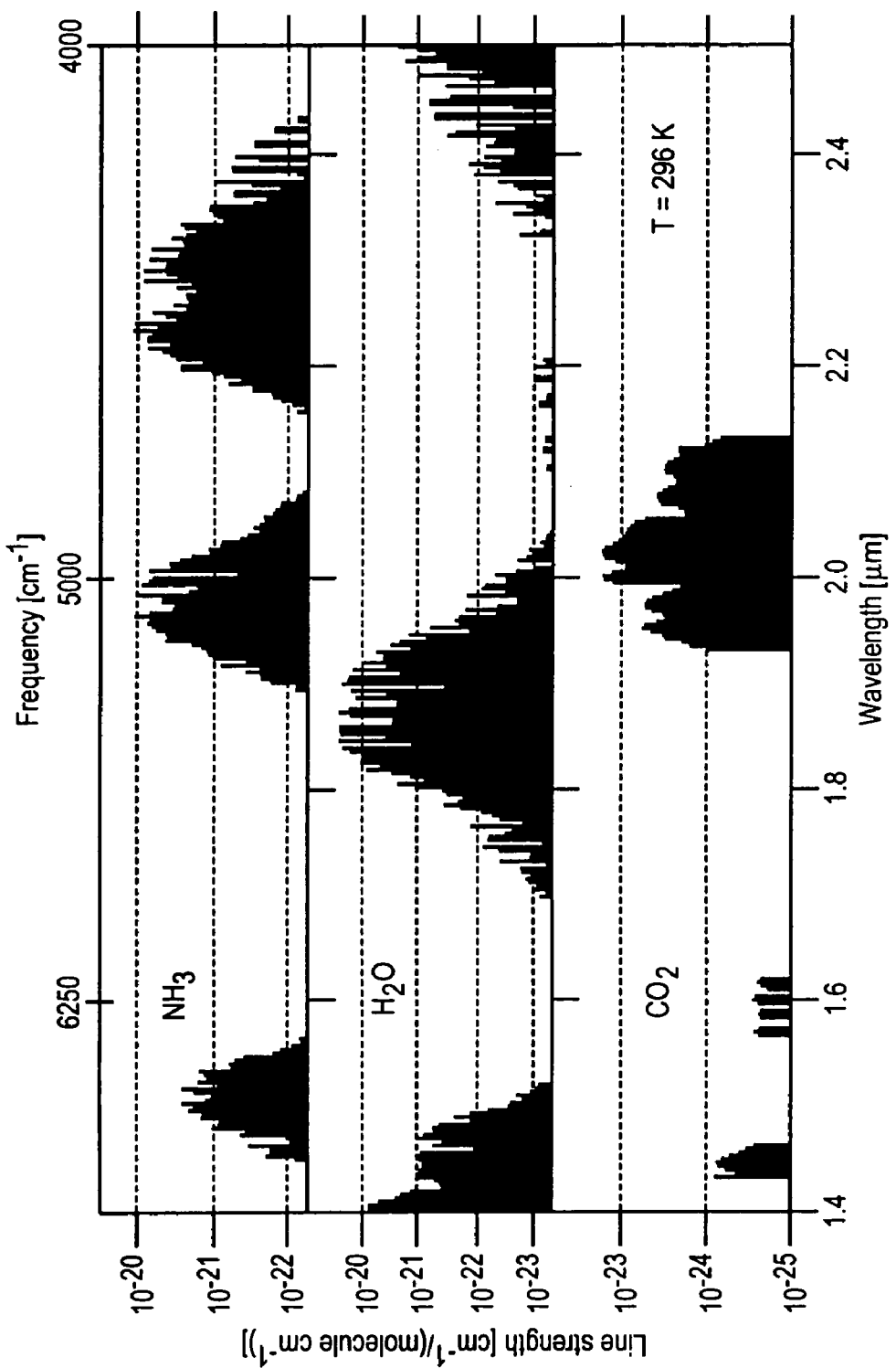
FIG. 11 compares the near infrared absorption bands of gaseous carbon dioxide with the near infrared absorption bands of water vapor.

In a like manner, FIG. 10 plots the correlation ($r^2$=0.908) between lower-resolution spectra, which were derived from the original spectra by processing them to reduce their resolution to 22 wavenumbers full width half maximum. This processing was done to simulate the spectra that might be obtained using a rotating interference filter, described in the present invention, instead of a lab spectrometer. Note that, at 3162 wavenumbers, the bandpass expressed in wavenumbers is exactly equal to the bandpass expressed in nanometers. At 3030 wavenumbers, a 22-wavenumber bandpass represents approximately a 20-nm bandpass. The present invention may also be used to detect CO2. As shown in FIG. 11, CO2 has bands of peaks near 1430 nm, 1575 nm, 1957 nm, 2007 nm, and 2057 nmm. Some of these overlap with water or hydrocarbon or other absorption peaks. A technique such as that of the present invention, which allows rapidly reading the on-peak versus off-peak absorbance may be able to resolve and quantify the peak regardless of such interferences.

Figure 4:
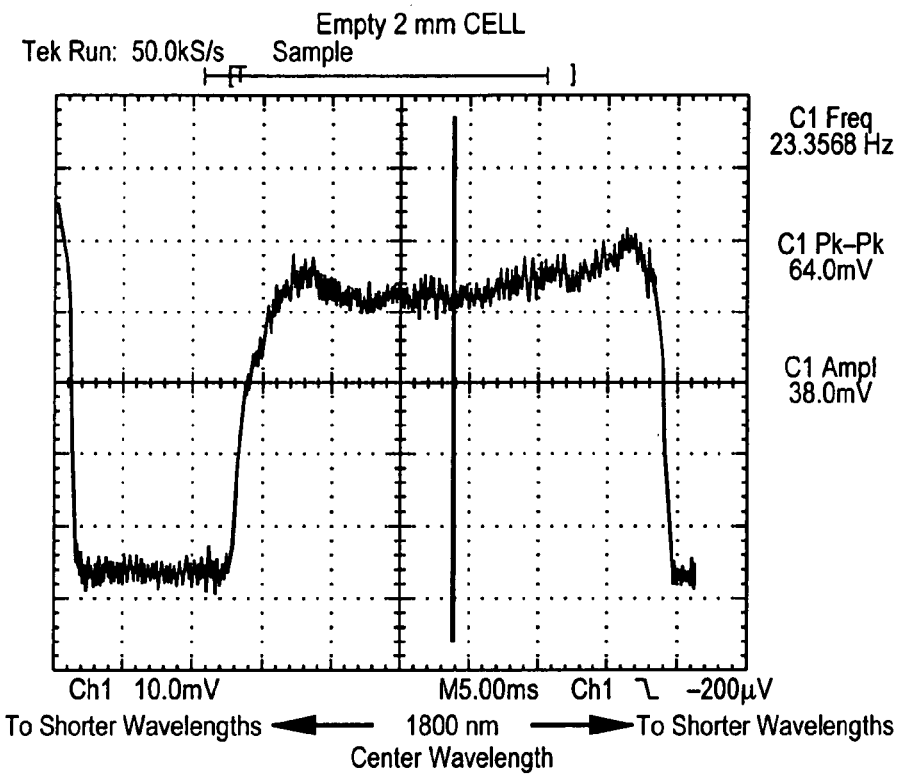
FIG. 4 illustrates an oscilloscope display for an empty 2 mm path length glass sample cell.

FIGS. 4-7 illustrate an example of data taken with a spinning filter apparatus in a laboratory. FIG. 4 shows an oscilloscope display for an empty 2 mm path length glass sample cell. The absorbance of the glass cell is both constant and negligible from 1700-1800 nm. However, the tungsten light source, which peaks in intensity around 1000 nm, continues to tail off in intensity in going from 1700 nm to 1800 nm. Indeed, the center wavelength (1800 nm) of the empty cell's raw spectrum is less than the intensity of wavelengths at either end (about 1700 nm) of the spectrum.

Figure 5:
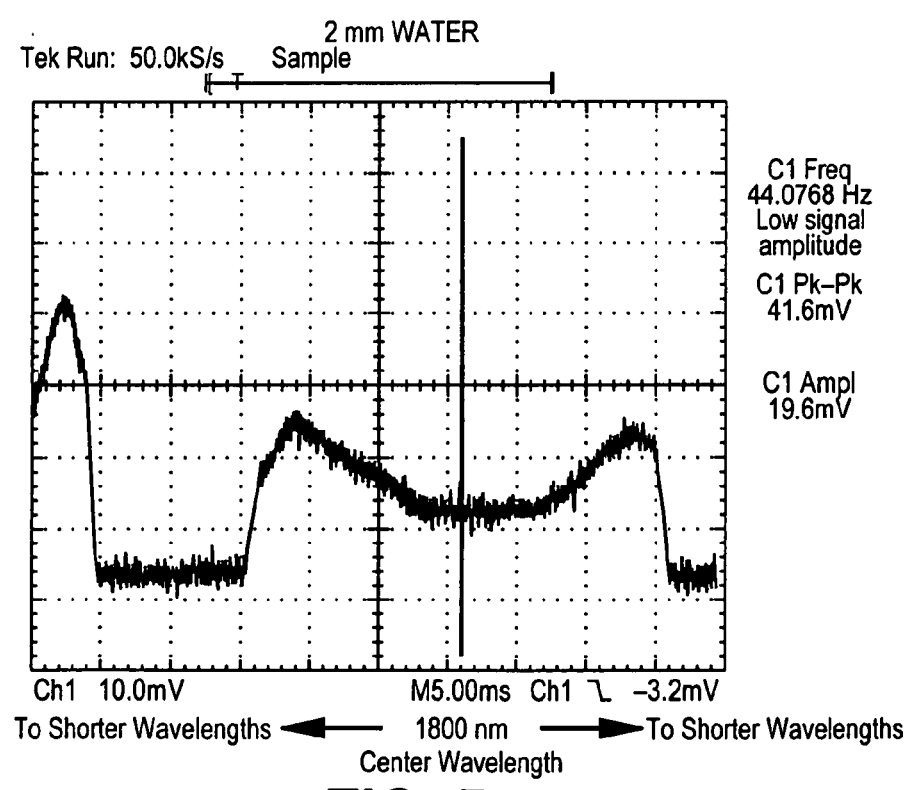
FIG. 5 illustrates an oscilloscope display for a 2 mm glass sample cell full of water.

FIG. 5 shows an oscilloscope display for a 2 mm glass sample cell full of water. Water has no major peaks between 1700 and 1800 nm. However, the region shown in FIG. 5 is at the tail end of a major water peak at 1930 nm. Consequently, water transmits less light at 1800 nm than at 1700 nm. The oscilloscope display shows a raw spectrum similar to the empty cell display except for a deeper central dip due to water being a little darker at 1800 nm than at 1700 nm.

Figure 6:
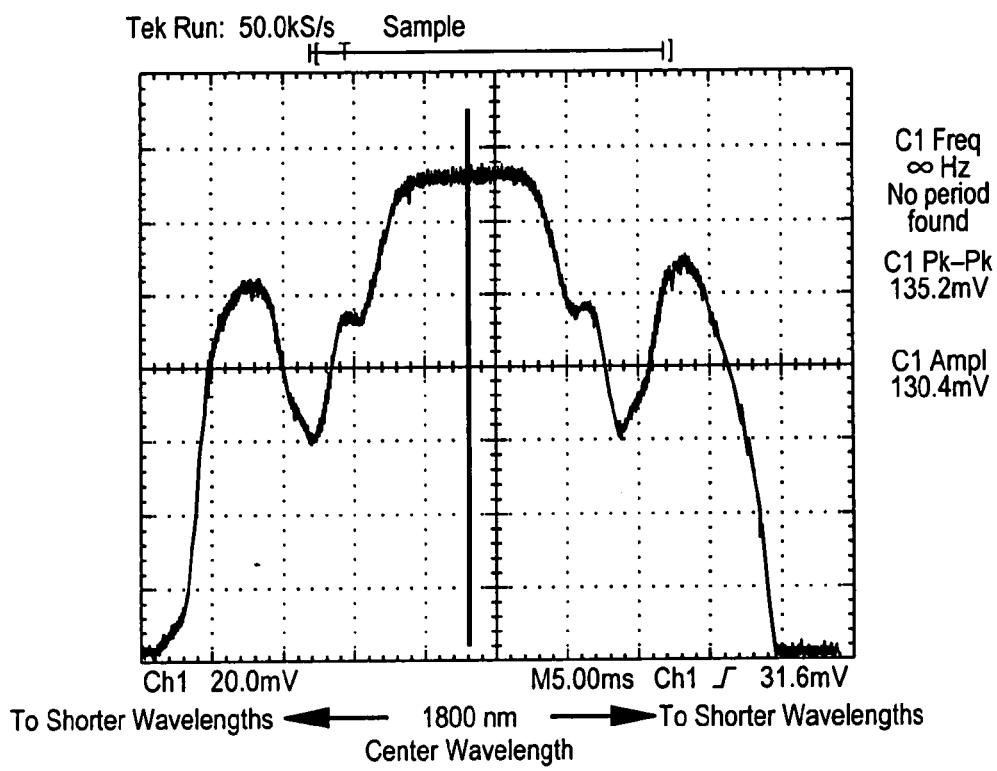
FIG. 6 illustrates an oscilloscope display for a 2 mm glass sample cell full of crude oil.

FIG. 6 shows an oscilloscope display for a 2 mm glass sample cell full of crude oil. Moving in either direction away from the center of the spectrum enables a user to see characteristic dips in the transmitted light intensity (absorbance peaks) corresponding to the spectral signature of hydrocarbons. These absorbance peaks occur near 1760 nm and 1725 nm.

Figure 7:
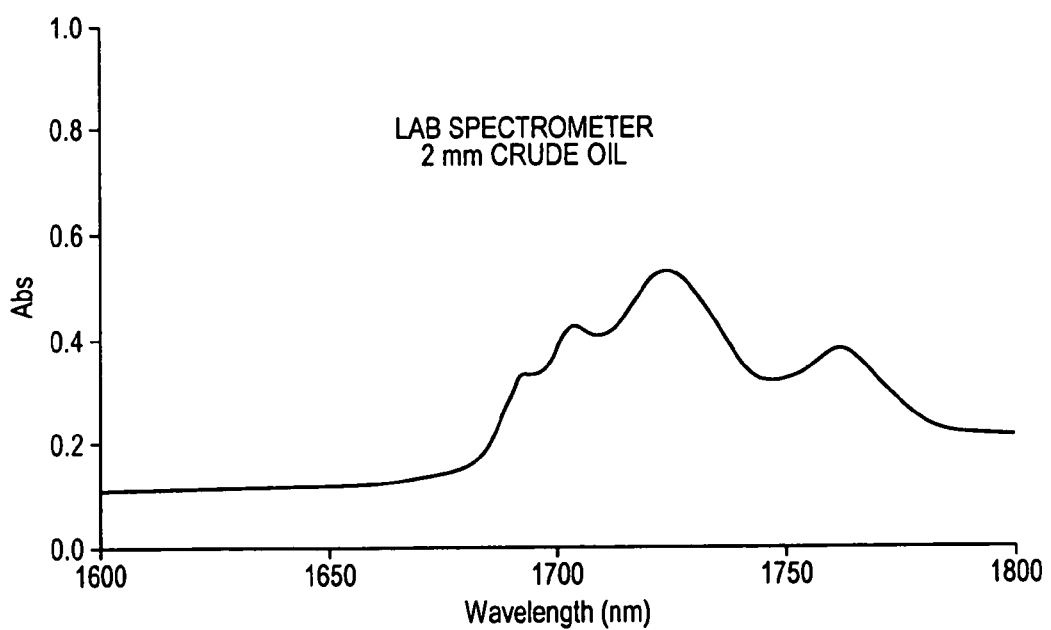
FIG. 7 illustrates a processed spectrum of the same crude oil taken on a research-grade Cary 500 laboratory spectrometer.

FIG. 7 shows a processed spectrum of the same crude oil taken on a research-grade Cary 500 laboratory spectrometer. The processing comprises correcting for the variation in the intensity of the light source at different wavelengths. A spectrum of the empty cell is collected first, followed by the spectrum of the cell filled with a sample. The base ten logarithm of the ratio of the empty cell light intensity to the sample-filled cell light intensity is the "absorbance" of the sample in the cell and is plotted on the y-axis. It is preferable to generate processed rather than raw spectra from data collected using the apparatus of the invention.

Comparing FIG. 6 to FIG. 7, the y-axis of each oscilloscope display is a linear scale with light increasing in the up direction and with no correction being made for variation in the intensity of the light source with wavelength. However, the y-axis of the Cary spectra is a logarithmic scale with light decreasing in the up direction and a correction being made for the variation in intensity of the light source with wavelength. Conceptually, turning the oscilloscope display upside down and compressing the y-axis, produces a curve very similar to the Cary spectra. The dips in the oscilloscope displays correspond to the peaks in the Cary displays. Despite these y-axis dissimilarities, the wavelength positions of the peaks in the Cary displays can be used to assign wavelengths to the time scale of the oscilloscope displays. Also, one can assign wavelengths to the time scale by knowing the angle of the rotating filter at each time (and the filter's normal-incidence center wavelength). For simplicity, we can provide a motor, which spins the filter at constant speed.

For one embodiment of the high-resolution spectrometer, wavelength coverage is continuous and the wavelength step size is selected to be as small as possible to measure the angle of rotation. Using an interference filter having a sufficiently narrow bandpass, it is possible to perform a high-resolution scan over one or more portions of the first overtone hydrocarbon band (1600-1850 nm) or over other interesting spectral features. These higher resolution spectra improve our ability to quantify chemical concentrations and to estimate any spectrally correlated physical properties. For example, a user can quantify the percentages of aromatics, olefins, and saturates in the crude oil and estimate the gas oil ratio (GOR) from the percentage of methane, whose peak at 1667 nm, lies left of heavier hydrocarbons peaks that are around 1700-1800 nm.

The spectrometer of the present invention is used in conjunction with a wire line formation tester (e.g. the Reservoir Characterization Instrument (RCI)). It would supplement the existing 17-channel downhole spectrometer, which currently monitors sample cleanup in real time.

With a high-resolution spectrometer, a user should be able to quantify a crude oil's percentage of aromatics, olefins, and saturates, to estimate its gas oil ratio (GOR). Gases such as $CO_2$ are detectable. With a proper training set, it is possible to develop a correlation equation for the percentage of oil-based mud filtrate contamination in the crude oil.

Figure 8:
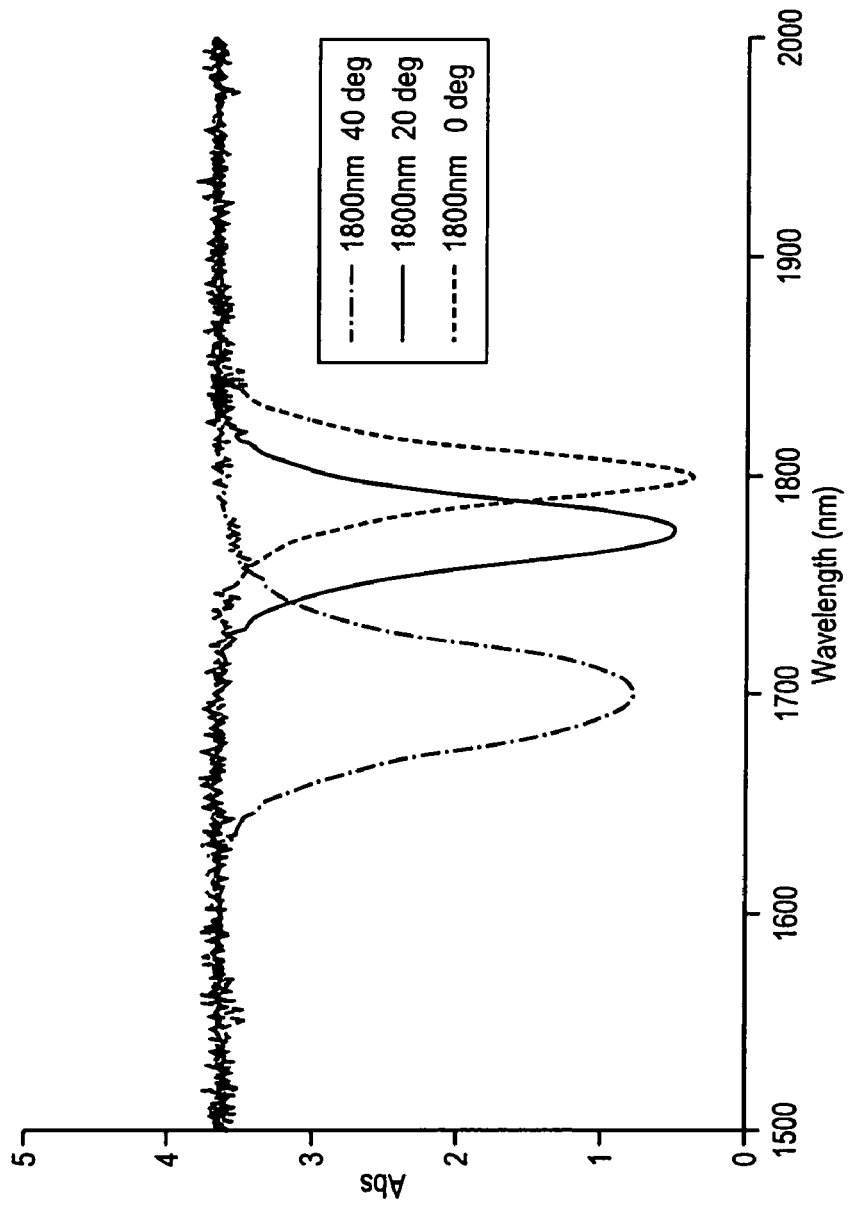
FIG. 8 illustrates how a Full Width at Half Maximum of the transmission of an 1800 nm filter changes with tilt.

Turning now to FIG. 8, FIG. 8 illustrates how the band pass (Full Width at Half Maximum of the transmission) of an 1800-nm filter changes with tilt. Note that one-half of the transmission corresponds to a 0.3 Absorbance increase because $-\log_{10}(½)=0.3$. As shown in FIG. 8, the greater the tilt angle, the more that the center wavelength shifts to shorter wavelengths and the broader the bandpass becomes about the new center wavelength. At 40 degrees from normal, FWHM=26 nm; at 20 degrees from normal, FWHM=16 nm; and at 0 degrees from normal, FWHM=11 nm. As shown in FIG. 8, the resolution bandwidth is proportional to the angular displacement of the interference filter with respect to the normal incidence of light from the sample.

Figure 12A:
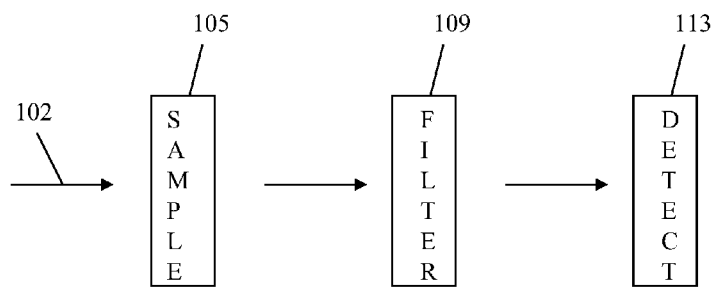
FIG. 12 is an illustration of pre-filtering and post filtering for absorbance and reflectance spectral data.
Figure 12B:
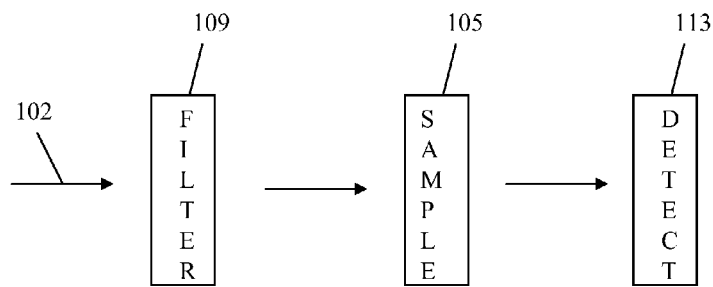
Figure 12C:
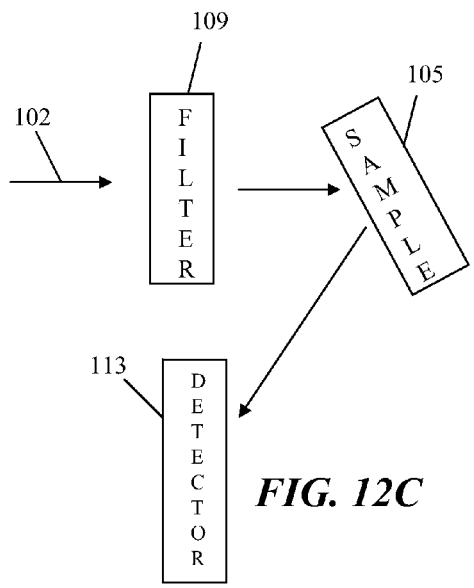
Figure 12D:
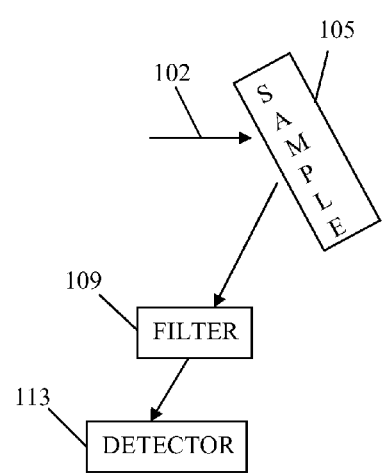

Turning now to FIG. 12, FIG. 12A illustrates post filtering by filter 109 of light 102 after it has passed through sample 105. The amount of light transmitted through the sample 105 (or absorbed by the sample) is measured by detector 113. FIG. 12A illustrates post filtering by filter 109 of light 102 after it has passed through sample 105. The amount of light transmitted through the sample (or absorbed by the sample) is measured by detector 113. FIG. 12c illustrates pre filtering by filter 109 of light 102 before it has passed through sample 105. The amount of light reflected off of the sample is measured by detector 113. FIG. 12d illustrates post filtering by filter 109 of light 102 after it has passed through sample 105. The amount of light reflected off of the sample is measured by detector 113.

The present invention has been described as a method and apparatus operating in an oil rig environment in the example embodiment, however, the present invention may also be embodied as a set of instructions on a computer readable medium, comprising ROM, RAM, CD ROM, Flash or any other computer readable medium, now known or unknown that when executed cause a computer to implement the method of the present invention. An example of an embodiment of the invention has been shown by the above example. This example, however, is for purposes of example only and not intended to limit the scope of the invention, which is defined by the following claims.

What is claimed is:

1. An apparatus for estimating a property of a downhole fluid comprising:

an interference filter that scans frequencies of light associated with the downhole fluid, wherein an angle of interference filter relative to the light varies;

a detector for detecting light scanned by the interference filter; and a processor for determining a spectral component of at least one of the scanned frequencies of the light to determine the property of the downhole fluid.

2. The apparatus of claim 1, further comprising:
a lens for receiving the scanned frequencies of light.

3. The apparatus of claim 1 further comprising:
a stepper motor to rotate the interference filter.

4. The apparatus of claim 1, the apparatus further comprising:
a baffle for optically isolating a filter-detector pair from a neighboring filter-detector pair wherein the filter comprises a plurality of filters and the detector comprises a plurality of detectors.

5. The apparatus of claim 1, further comprising:
a lens to capture light exiting the interference filter despite beam offset associated with the interference filter.

6. The apparatus of claim 1, further comprising:
a holder for supporting at least one interference filter during rotation.

7. The apparatus of claim 1, wherein the interference filter is positioned so that the light is filtered by the interference filter before it is incident on the fluid.

8. The apparatus of claim 7, wherein the detector is positioned so that the light passes through the fluid before it is detected.

9. The apparatus of claim 7, wherein the detector is positioned so that the light is reflected off of the fluid before it is detected.

10. The apparatus of claim 1, wherein the filter is positioned so that light is filtered after it is incident on the fluid.

11. The apparatus of claim 10, wherein the detector is positioned so that light is detected after the light passes through the fluid.

12. The apparatus of claim 10, wherein the detector is positioned so that light is detected after the light is reflected off of the fluid.

13. The apparatus of claim 1, further comprising:
wherein the spectral component is associated with a gas.

14. A method for estimating a property of a fluid comprising:
obtaining a fluid extracted from an earth formation by a downhole tool; exposing the fluid to light;
passing the light through a rotating interference filter;
detecting intensity of the light associated with the fluid;
estimating the property of the fluid from the measured intensity of light associated with the fluid and an angle of the interference filter; and
recording the estimated property of the fluid on a suitable medium.

15. The method of claim 14, wherein detecting intensity of light further comprises gathering the light.

16. The method of claim 14, further comprising:
detecting an angle of rotation for the rotating interference filter.

17. The method of claim 14, wherein detecting the intensity of light further comprises:
optically isolating the interference filter and a detector pair from a neighboring filter and a detector pair.

18. The method of claim 15, further comprising:
using a lens to gather the light.

19. The method of claim 14, further comprising:
filtering the light before the light is incident on the fluid.

20. The method of claim 19, further comprising:
detecting the light after the light passes through the fluid.

21. The method of claim 19, further comprising:
detecting the light reflected off of the fluid.

22. The method of claim 14, further comprising:
filtering the light after it is incident on the fluid.

23. The method of claim 22, further comprising:
detecting the light after it passes through the fluid.

24. The method of claim 22, further comprising:
detecting the light reflected off of the fluid.

25. The method of claim 14, further comprising:
deriving a wavelength of scanned light from an angle of rotation for the interference filter.

26. The method of claim 14, further comprising:
scanning a fluid spectrum by measuring at a plurality of angles of rotation at least one of the light transmitted through the fluid and the light reflected off of the fluid.

27. The method of claim 14, further comprising:
scanning four spectral scans with rotation of the interference filter at selected angles of incidence.

28. The method of claim 27, further comprising:
gating the four spectral scans to select at least one of the set consisting of a single scan and an average of at least two spectral scans.

29. The method of claim 14, wherein passing the light through the rotating filter further comprises:
rotating the interference filter freely on a spindle.

30. The method of claim 14, wherein passing the light through the rotating filter further comprises:
angularly oscillating the interference filter about a central angle.

31. The method of claim 14, further comprising:
stepping an angular rotation of the interference filter between two positions in order to obtain an on-peak versus off-peak wavelength.

32. The method of claim 14, further comprising:
holding the interference filter by an edge of the filter so that the holder does not create a shadow at a filter center of rotation.

33. The method of claim 14, further comprising
determining a gas oil ratio by estimating a percentage of methane in the fluid.

34. The method of claim 14, further comprising:
determining a percentage of at least one the set consisting of aromatics, olefins, saturates in the fluid.

35. The method of claim 14, further comprising:
determining a percentage of contamination from the property of the fluid and an equation developed by correlation to a training set and the property of the fluid.

36. The method of claim 14, further comprising:
determining a percentage of $CO_2$ in natural gas in the fluid.

37. The method of claim 14, further comprising:
determining a percentage of contamination using high-resolution spectra downhole to monitor sample cleanup.

38. The method of claim 14, further comprising:
determining a percentage of aromatics to monitor sample cleanup.

39. A system for determining a property of a downhole fluid comprising:
a downhole tool comprising a rotating interference filter that scans frequencies of light associated with the downhole fluid;
a light-detecting device in the downhole tool for detecting light scanned by the rotating interference filter; and
a processor for determining a spectral component of at least one of the scanned frequencies of the light to determine the property of the downhole fluid.

* * * * *

UNITED STATES PATENT AND TRADEMARK OFFICE
CERTIFICATE OF CORRECTION

| | | |
|---|---|---|
| PATENT NO. | : 7,280,214 B2 | Page 1 of 1 |
| APPLICATION NO. | : 10/827948 | |
| DATED | : October 9, 2007 | |
| INVENTOR(S) | : Rocco DiFoggio, Arnold Walkow and Paul Bergren | |

It is certified that error appears in the above-identified patent and that said Letters Patent is hereby corrected as shown below:

Column 4, line 30, change "FIG. 12 is an illustration of" to --FIGS. 12A-D illustrate--;

Column 10, line 31, change "Turning now to FIG. 12" to --Turning now to FIGS. 12A-D--;

Column 10, line 62, change "interference filter" to --the interference filter--;

Column 10, line 67, change "determine" to --estimate--;

Column 11, line 5, change "claim 1, the apparatus further" to --claim 1 further--;

Column 11, line 34, change "claim 1, further comprising:" to --claim 1,--;

Column 12, line 27, change "the rotating filter" to --the rotating interference filter--;

Column 12, line 38, change "at least one the set" to --at least one from the set--;

Column 12, line 39, change "of aromatics, olefins, saturates in the fluid" to --of: aromatics, olefins, and saturates in the fluid--.

Signed and Sealed this

Tenth Day of June, 2008

JON W. DUDAS
*Director of the United States Patent and Trademark Office*